US00PP18349P2

(12) United States Plant Patent
Lowe

(10) Patent No.: US PP18,349 P2
(45) Date of Patent: Dec. 25, 2007

(54) ***GERANIUM* PLANT NAMED 'INDY RED'**

(50) Latin Name: *Geranium cinereum*
Varietal Denomination: Indy Red

(75) Inventor: Carl Lowe, Holsworthy (GB)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/494,093

(22) Filed: Jul. 27, 2006

(51) Int. Cl.
*A01H 5/00* (2006.01)

(52) U.S. Cl. ..... Plt./324
(58) Field of Classification Search ..... Plt./324
See application file for complete search history.

*Primary Examiner*—Kent Bell
(74) *Attorney, Agent, or Firm*—C. A. Whealy

(57) ABSTRACT

A new and distinct cultivar of *Geranium* plant named 'Indy Red', characterized by its upright and outwardly spreading plant habit; freely basal branching habit; dark green-colored leaves; freely flowering habit; intense red purple-colored flowers; and good garden performance.

2 Drawing Sheets

Botanical designation: *Geranium cinereum.*
Cultivar denomination: 'Indy Red'.

BACKGROUND OF THE INVENTION

The present invention relates to a new and distinct cultivar of *Geranium,* botanically known as *Geranium cinereum,* and hereinafter referred to by the name 'Indy Red'.

The new *Geranium* originated from an open-pollination of an unnamed selection of *Geranium cinereum,* not patented, as the female, or seed, parent with an unknown selection of *Geranium cinereum,* as the male, or pollen, parent. The new *Geranium* was discovered and selected by the Inventor as a single flowering plant from within the progeny of the stated open-pollination grown in a controlled environment in Shropshire, United Kingdom in 2002.

Asexual reproduction of the new *Geranium* by softwood terminal cuttings in a controlled environment in Shropshire, United Kingdom since 2003, has shown that the unique features of this new *Geranium* are stable and reproduced true to type in successive generations.

SUMMARY OF THE INVENTION

The cultivar 'Indy Red' has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Indy Red'. These characteristics in combination distinguish 'Indy Red' as a new and distinct cultivar of *Geranium:*

1. Upright and outwardly spreading plant habit.
2. Freely basal branching habit.
3. Dark green-colored leaves.
4. Freely flowering habit.
5. Intense red purple-colored flowers.
6. Good garden performance.

Plants of the new *Geranium* differ primarily from plants of the parent selections in plant size and flower color.

Plants of the new *Geranium* can be compared to plants of the *Geranium cinereum* cultivar Carol, disclosed in U.S. Plant Pat. No. 14,124. In side-by-side comparisons conducted in Lisserbroek, The Netherlands, plant of the new *Geranium* differed primarily from plants of the cultivar Carol in flower color as plants of the cultivar Carol had purple-colored flowers.

BRIEF DESCRIPTION OF THE PHOTOGRAPHS

The accompanying colored photographs illustrate the overall appearance of the new *Geranium,* showing the colors as true as it is reasonably possible to obtain in colored reproductions of this type. Colors in the photographs may differ slightly from the color values cited in the detailed botanical description which accurately describe the colors of the new *Geranium.*

The photograph on the first sheet comprises a side perspective view of a typical flowering plant of 'Indy Red' grown in a container.

The photograph at the top of the second sheet is a close-up view of typical flowers of 'Indy Red'.

The photograph at the bottom of the second sheet is a close-up view of a typical leaf of 'Indy Red'.

DETAILED BOTANICAL DESCRIPTION

The photographs and following observations, measurements and values describe plants grown in Lisserbroek, The Netherlands in an outdoor nursery during the summer. During the production of the plants, day temperatures ranged from 14° C. to 32° C., night temperatures ranged from 7° C. to 15° C. and light levels ranged from 10,000 lux to 50,000 lux. Plants were about two years old when the photographs and the description were taken. In the detailed description, color references are made to The Royal Horticultural Society Colour Chart, 2001 Edition, except where general terms of ordinary dictionary significance are used.

Botanical classification: *Geranium cinereum* cultivar 'Indy Red'.

Parentage:

*Female, or seed, parent.*—Unnamed selection of *Geranium cinereum,* not patented.

*Male or pollen parent.*—Unknown selection of *Geranium cinereum.*

Propagation:

*Type.*—By softwood cuttings.

*Time to initiate roots.*—About 20 to 30 days at temperatures of 18° C.

*Time to produce a rooted young plant.*—About 100 days at temperatures of 22° C.

*Root description.*—Fine, moderately fibrous; light grey to brown in color.

*Rooting habit.*—Freely branching, moderately dense.

Plant description:

*General appearance.*—Upright and outwardly spreading plant habit; broad inverted triangle.

*Growth and branching habit.*—Moderately vigorous growth habit. Freely basal branching habit with about 13 lateral branches per plant.

*Plant height, to top of umbels.*—About 20 cm.

*Plant width.*—About 29.3 cm.

*Lateral branches.*—Length: About 16.2 cm. Diameter: About 1.5 mm. Internode length: About 8.5 cm. Texture: Pubescent. Strength: Moderately strong. Color: 143A to 143B.

Foliage description:

*Arrangement.*—Basal and alternate; simple.

*Length.*—About 3.4 cm.

*Width.*—About 3.9 cm.

*Shape.*—Orbicular.

*Apex.*—Acute.

*Base.*—Hastate.

*Margin.*—Palmately cleft; lobes crenate.

*Venation pattern.*—Palmate.

*Texture, upper surface.*—Pubescent.

*Texture, lower surface.*—Smooth, glabrous.

*Color.*—Developing foliage, upper surface: 137A. Developing foliage, lower surface: 137C. Fully developed, upper surface: 137A to 139A; venation, 143B. Fully developed, lower surface: 137C; venation, 137D.

*Petiole.*—Length: About 13.1 cm. Diameter: About 1.2 mm. Texture, upper and lower surfaces: Pubescent. Color, upper and lower surfaces: 143A to 143B.

Flower description:

*Flower arrangement.*—Single rotate flowers arranged in pairs arising from apical leaf axils. Flowers face upright to slightly outward. Flowers not persistent. Flowers not fragrant.

*Quantity of flowers.*—Freely flowering habit; about 16 flower buds and open flowers per lateral branch.

*Flowering season.*—In The Netherlands, flowering is continuous from late spring to late summer.

*Flower longevity.*—Flowers last about one week on the plant.

*Flower diameter.*—About 2.8 cm.

*Flower depth* (*height*).—About 1.1 cm.

*Flower buds.*—Length: About 8 mm. Diameter: About 5 mm. Shape: Elliptic to obovate. Color: 137A.

*Petals.*—Quantity per flower: Five in a single whorl. Length: About 1.5 cm. Width: About 1.2 cm. Shape: Obcordate. Apex: Emarginate. Base: Attenuate. Margin: Entire. Texture, upper and lower surfaces: Mostly smooth; towards the base, densely pubescent. Color: When opening and fully opened, upper surface: N60C to 61B; towards the base, 83D; venation, N79A. When opening and fully opened, lower surface: N60D; towards the base, 83D; venation, N79A.

*Sepals.*—Quantity per flower: Five, arranged in a single whorl. Length: About 9 mm. Width: About 4 mm. Shape: Obovate. Apex: Aristate. Base: Cuneate. Margin: Entire. Texture, upper and lower surfaces: Densely pubescent. Color: When opening and fully opened, upper surface: 137A to 137B. When opening and fully opened, lower surface: 143A.

*Peduncles.*—Length: About 4.6 cm. Diameter: About 1 mm. Strength: Moderately strong. Angle: About 10° C. from vertical. Texture: Pubescent. Color: 143A to 143B.

*Pedicels.*—Length: About 2.4 cm. Diameter: About 8 mm. Strength: Moderately strong. Angle: About 25° C. from vertical. Texture: Pubescent. Color: 143B.

*Reproductive organs.*—Androecium: Stamen quantity per flower: About ten. Filament length: About 3 mm. Filament color: N79C. Anther length: About 2 mm. Anther shape: Oblong. Anther color: N186A to 202A. Pollen amount: Scarce. Pollen color: N186A. Gynoecium: Pistil quantity per flower: One. Pistil length: About 4 mm. Stigma shape: Five-parted; reflexed. Stigma color: N79B to N79C. Style length: About 3 mm. Style color: 144A. Ovary color: 141C.

*Seed.*—Seed development has not been observed.

Disease/pest resistance: Plants of the new *Geranium* have not been observed to be resistant to pathogens and pests common to *Geraniums.*

Garden performance: Plants of the new *Geranium* have exhibited good tolerance to rain and wind and have been observed to be suitable for USDA Zones 5 to 9.

It is claimed:

1. A new and distinct *Geranium* plant named 'Indy Red' as illustrated and described.

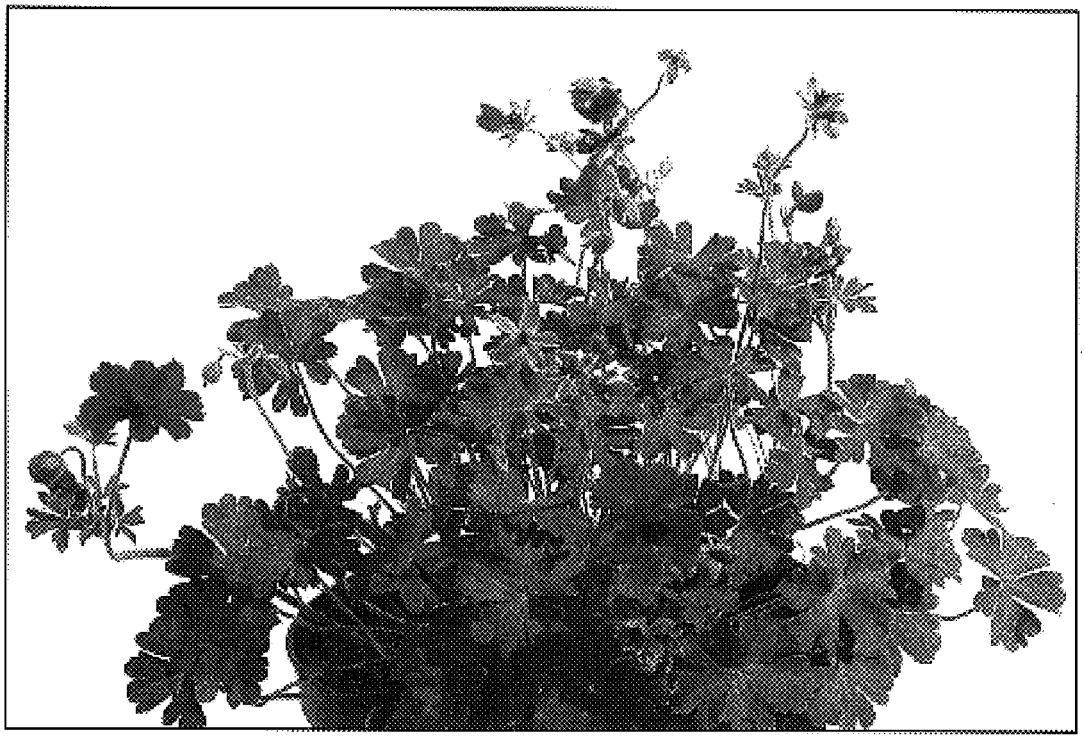

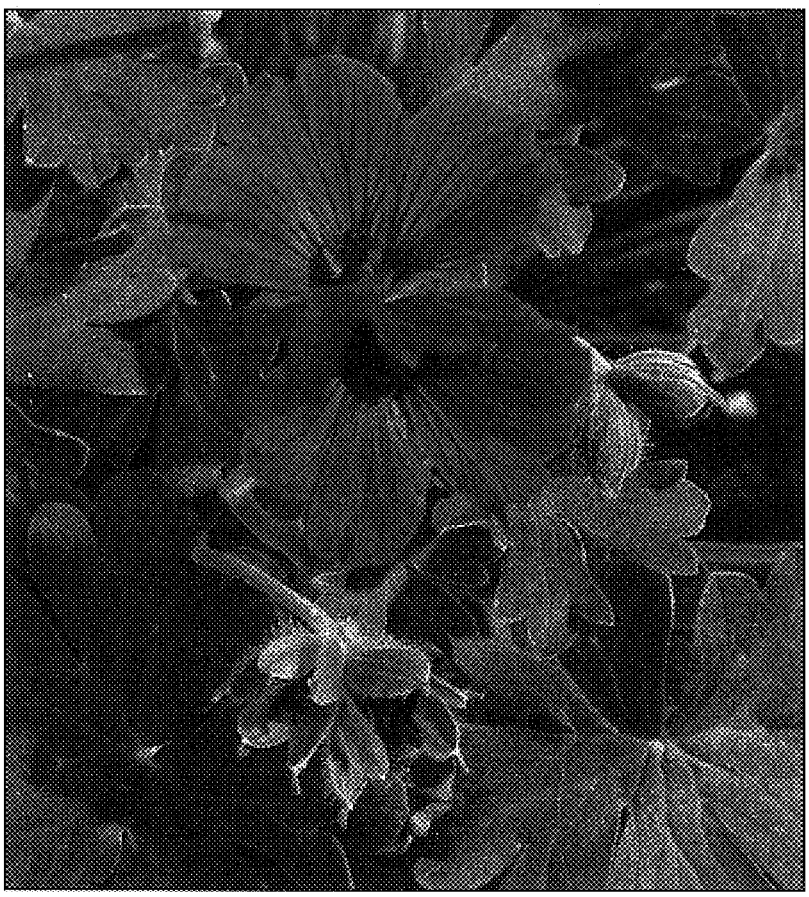
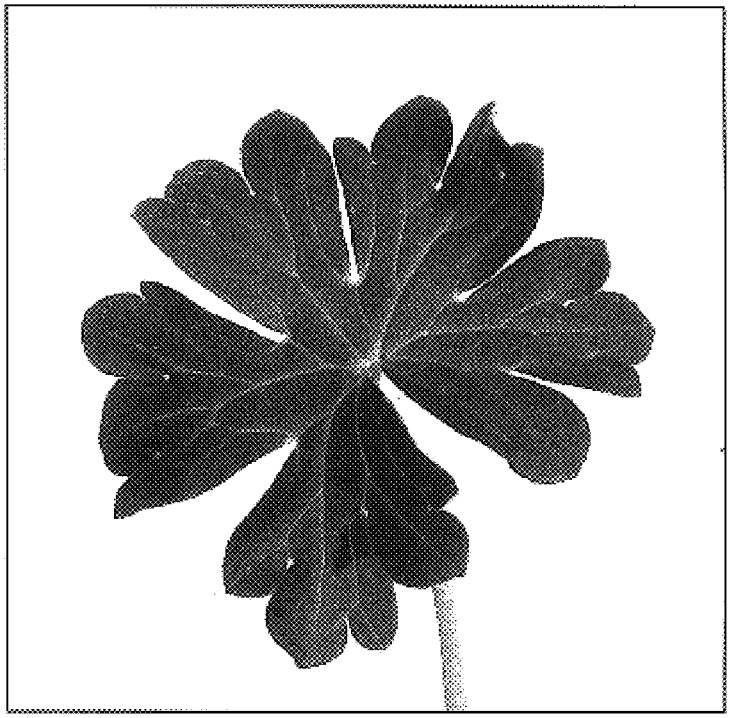

* * * * *